United States Patent
Stambeck (10) Patent No.: US 11,317,827 B2
(45) Date of Patent: May 3, 2022

(54) PORTABLE SAMPLING DEVICE, STAND AND METHOD FOR COLLECTING PARTICLES FROM EXHALED BREATH

(71) Applicant: MUNKPLAST AB, Uppsala (SE)

(72) Inventor: Peter Stambeck, Björklinge (SE)

(73) Assignee: MUNKPLAST AB, Uppsala (SE)

( * ) Notice: Subject to any disclaimer, the term of this patent is extended or adjusted under 35 U.S.C. 154(b) by 352 days.

(21) Appl. No.: 15/986,883

(22) Filed: May 23, 2018

(65) Prior Publication Data
US 2018/0263531 A1  Sep. 20, 2018

Related U.S. Application Data
(63) Continuation of application No. PCT/SE2016/051159, filed on Nov. 23, 2016.

(30) Foreign Application Priority Data

Nov. 24, 2015 (SE) .................................... 1551526-5

(51) Int. Cl.
*A61B 5/097* (2006.01)
*G01N 33/497* (2006.01)
(Continued)

(52) U.S. Cl.
CPC .............. *A61B 5/097* (2013.01); *A61B 5/082* (2013.01); *G01N 33/497* (2013.01); *A61B 2010/0087* (2013.01)

(58) Field of Classification Search
CPC . A61B 5/097; A61B 5/082; A61B 2010/0087; G01N 33/497
(Continued)

(56) References Cited

U.S. PATENT DOCUMENTS

| | | | |
|---|---|---|---|
| 5,787,884 A | 8/1998 | Tovey | |
| 6,733,464 B2 * | 5/2004 | Olbrich | A61B 5/411 600/538 |

(Continued)

FOREIGN PATENT DOCUMENTS

| | | |
|---|---|---|
| EP | 1394528 A3 | 3/2004 |
| EP | 2781917 A1 | 9/2014 |

OTHER PUBLICATIONS

Katharina Schwarz, et al., "Characterization of exhaled particles from the healthy human lung—a systematic analysis in relation to pulmonary function variables", J Aerosol Med Pulm Drug Del. Dec. 2010; 23(6):371-9. doi: 10.1089/jamp.2009.009. Epub May 25, 2010.

(Continued)

*Primary Examiner* — Jacqueline Cheng
*Assistant Examiner* — Tho Q Tran
(74) *Attorney, Agent, or Firm* — Reising Ethington P.C.

(57) ABSTRACT

A portable sampling device (1) for collecting particles in a stream of exhaled breath comprising a housing (10) with an inlet (11) and an outlet (12) arranged to guide the stream of exhaled breath therethrough, a collecting device holder (20) arranged at least partially inside the housing and comprising at least one flow path (21) in fluid connection with the inlet in which a collecting device (30) is arranged, the collecting device being adapted to collect the particles in the exhaled breath, wherein the collecting device has a diameter smaller than the flow path diameter and is movably arranged in the collecting device holder.

11 Claims, 7 Drawing Sheets

(51) Int. Cl.
  *A61B 5/08* (2006.01)
  *A61B 10/00* (2006.01)
(58) Field of Classification Search
  USPC .......................................................... 600/543
  See application file for complete search history.

(56) References Cited

U.S. PATENT DOCUMENTS

| | | | | |
|---|---|---|---|---|
| 8,030,088 | B2* | 10/2011 | McCash | A61B 5/097 |
| | | | | 436/164 |
| 9,918,661 | B2* | 3/2018 | Cormier | A61B 5/082 |
| 2004/0161804 | A1* | 8/2004 | McCash | A61B 5/097 |
| | | | | 435/7.2 |
| 2005/0177057 | A1* | 8/2005 | Friedman | A61B 5/097 |
| | | | | 600/543 |
| 2005/0184264 | A1* | 8/2005 | Tesluk | A61M 39/105 |
| | | | | 251/148 |
| 2008/0092629 | A1* | 4/2008 | Suga | A61B 5/097 |
| | | | | 73/28.05 |
| 2014/0288454 | A1* | 9/2014 | Paz | A61B 5/4845 |
| | | | | 600/532 |
| 2016/0299125 | A1* | 10/2016 | Cristoni | G01N 1/2205 |

OTHER PUBLICATIONS

Olof Beck et al., "Demonstration that methadone is being present in the exhaled breath aerosol fraction", Journal of Pharmaceutical and Biomedical Analysis 56(2011) 1024.1028. E-pb Aug. 9, 2011.

* cited by examiner

PORTABLE SAMPLING DEVICE, STAND AND METHOD FOR COLLECTING PARTICLES FROM EXHALED BREATH

This application is the continuation of International Application No. PCT/SE2016/051159, filed 23 Nov. 2016, which claims the benefit of Swedish Patent Application No. SE 1551526-5, filed 24 Nov. 2015, the entire contents of which are hereby incorporated by reference.

TECHNICAL FIELD

The present invention relates generally to a portable sampling device for collecting particles in a flow of exhaled breath from a user, a stand for such a portable sampling device and a method for collecting particles in a flow of exhaled breath from a user using such a device. Said particles may be aerosol particles formed or found in the alveoli of the lungs, such as biomarkers or exogenous compounds containing traces of drugs or other substances.

BACKGROUND ART

Human breath contains aerosol particles that are formed from the respiratory tract lining fluid covering the airways during normal breathing. Said particles have a size of between 0.1 and 2 µm, with an average size of between 0.3 and 0.8 µm. See article "Characterization of Exhaled particles from the Healthy Human Lung", *Journal of aerosol medicine and pulmonary drug delivery*, Volume 23, Number 6, 2010 by Schwarz et al. The aerosol particles carry non-volatile components containing diagnostic information or biomarkers and are often studied as the breath condensate fraction. In this aerosol fraction, both lipids and peptides of endogenous origin have been demonstrated. It has also been discovered that exogenous compounds are present in the exhaled breath. Such exogenous compound may for example be drugs and narcotics. The respiratory tract lining fluid contain large quantities of antioxidants and surfactant. The surfactant phase is lipophilic and may represent a compartment for the exogenous compounds. Thus, exhaled breath can be used as a matrix for several types of testing such as for example testing of a medical condition or a medical treatment procedure, abused drug testing or doping testing. It can also be used for medical research.

With the discovery of exogenous aerosol particles present in exhaled breath, a need for new methods and devices for collecting and analysing said aerosol particles in exhaled breath has arisen. For accurate analyse it is of importance that as many of the aerosol particles as possible is collected from a sample breath. Further, in some applications, such as for example testing for drug abuse or doping, the collection of particles is performed away from a lab environment. However, there is a lack of methods and devices for easy collection of said aerosol particles in exhaled breath.

It is also previously known to collect aerosol particles in exhaled breath using different types of filters. In an article published in the *Journal of Pharm Biomed Anal.* 2011 Dec. 15; 56(5):1024-8. doi: 10.1016/j.jpba.2011.08.004 (Epub 2011 Aug. 9) with title "Demonstration that methadone is being present in the exhaled breath aerosol fraction" two type of filters are tested when collecting aerosol particles for analysis of methadone in exhaled breath. Said two type of filters were a glass fibre filter and a polymer filter which where compared with an earlier used C18 silica filter. The polymer filter collected more than 90% of the aerosol particles in the exhaled breath. The polymer filter also has the practical advantage of having a low flow resistance making it possible to sample without pumping assistance. However, extracting the collected particles from a polymer filter is a complex process requiring a large amount of extraction fluid to separate the particles from the filter fibres.

WO 2012/120140 discloses a portable sampling device for collecting a sample from exhaled breath of a subject, the sampling device comprising a housing having at least one inlet and at least one outlet for the exhaled breath to exit through, and a sampling membrane arranged in the housing to collect aerosols from the exhaled breath. After a sample has been collected, the sampling membrane is removed from the housing and the collected aerosols and particles are extracted by immersing the sampling membrane in a suitable solvent. The removal of the sampling membrane is cumbersome and requires handling which may contaminate the sample, due to the flexible nature of the synthetic filter fibres and the way the sampling membrane is fastened to the housing (melted edge, separate support structure etc.).

Thus, there is a need to improve the prior art devices for collecting biomarkers, surfactant and other particles in exhaled air. Particularly, there is a need to provide sampling devices and methods which facilitate handling of the collected aerosol samples and reduce the risk of contamination.

SUMMARY OF THE INVENTION

An object of the present invention is to overcome the problems encountered by the available prior art as outlined above. In a first aspect of the present invention, there is provided a portable sampling device for collecting particles in a stream of exhaled breath provided with an inlet and an outlet. The sampling device further comprises a housing and a collecting device holder removably arranged at least partially inside the housing, wherein the housing and collecting device holder are arranged to guide the stream of exhaled breath through the device from the inlet to the outlet. Said collecting device holder comprising at least two flow paths in fluid connection with the inlet, wherein a collecting device is arranged in each flow path, the collecting device being adapted to collect the particles in the exhaled breath, wherein the collecting device has a diameter smaller than the flow path diameter and is movably arranged in the collecting device holder.

By providing a collecting device movably arranged in a flow path of the collecting device holder, the present invention facilitates handling of the collecting device, once the sample from the exhaled breath of the user has been collected. In the context of the present invention, the term "movably arranged" should be interpreted such that the collecting device is free to move with respect to the holder, e.g. by the effect of gravity. Medical personnel conducting the sampling procedure need not handle the collecting device directly with their hands, since the collecting device is easily removable from the collecting device holder by the effect of gravity.

In a preferred embodiment, the collecting device is movably arranged in a direction parallel to the flow path in the collecting device holder. This design allows for simple construction and optimal flow of exhaled breath through the collecting device in the flow path to further increase the amount of collected particles in the sampling device.

By providing at least two, preferably at least three, separate flow paths with each having a collecting device movably arranged therein, it is possible to take several samples from one exhaled breath of the user under identical conditions. This allows for multiple opportunities for analysing identical samples, for example at different times, or by different laboratories for verifying the analysis results. When three flow paths are provided one sample may be analysed at present, one sample is a reference and the third sample may be stored for future reference.

In an alternative embodiment, the portable sampling device further comprises means for retaining the collecting device in an upstream direction in the flow path of the collecting device holder. Preferably, the flow path has a cylindrical shape and the retaining means comprises an inwardly directed flange at a proximal end of the flow path. By providing retaining means, in the shape of an inwardly directed flange at a distal end of the flow path, the collecting device is held in the collecting device holder place during assembly.

In a further preferred embodiment, the housing comprises an abutment member adapted to abut against a distal end of the collecting device when the collecting device holder is arranged inside the housing. The abutment member of the housing works together with the retaining flange in the flow path of the collecting device holder to fix the collecting device in position in the flow path when the portable sampling device is assembled. This ensures that the collecting device remains in place during sampling.

In an advantageous embodiment, the portable sampling device further comprises corresponding locking means arranged on the housing and the collecting device holder, respectively. Preferably, the locking means comprises a cantilever snap-fit connection including at least one deflectable tab comprising a recess arranged on the housing and at least one cantilevered protrusion arranged on the collecting device holder, wherein the at least one protrusion is adapted to mate with and engage the recess in the at least one deflectable tab when the housing and the collecting device holder are brought together. By providing locking means, e.g. in the form of a snap-fit connection, a fast and secure attachment of the housing and the collecting device holder is achieved which ensures that any manipulation of or tampering with the sampling device is immediately noticed during any step of taking and preparing a sample from an exhaled breath of a user. Thus, it can be ensured that the sampling device remains intact during the entire process from manufacture and assembly to collecting a sample and analysing the sample.

In a preferred embodiment, the portable sampling device further comprises at least one lid to cover the inlet and/or the outlet of the sampling device. The lid(s) prevent contamination of the interior of the sampling device before and after use. Preferably, the at least one lid comprises at least one outwardly directed flange for easy removal.

In an alternative embodiment, the portable sampling device is disposable. To this end, the sampling device is made from an inexpensive, medically acceptable material such as plastic, preferably polypropylene (PP), polyvinylidene fluoride (PVDF), fluorinated ethylene propylene (FEP) and/or polytetrafluoroethylene (PTFE). The material is chosen to minimise or eliminate any reaction or interaction between the collected aerosol particles and the sampling device.

In a second aspect of the present invention, there is provided a stand for a portable sampling device according to the first aspect and adapted to hold at least one receptacle coaxially aligned with the at least one flow path of the collecting device holder, wherein the stand is movable between a first position and a second position, wherein in the first position the at least one collecting device is arranged in the collecting device holder, and in the second position the at least one collecting device is transferred to the at least one receptacle by means of gravity.

The stand further facilitates handling of the sample collected by the portable sampling device in that it provides a quick and simple way of transferring the collecting device containing the collected particles from the portable sampling device into a suitable receptacle, such as a test tube, a collection container with a closable lid or any other container adapted to hold a fluid sample and receive the collecting device. Medical personnel need not handle the collecting device directly, either by hand or using special tools. This minimises the risk of contamination or mishandling of the sample and the sample is transferred directly to a receptacle adapted for analysis, thus eliminating any intermediate transfer or preparation steps.

In a preferred embodiment, the stand comprises a rack portion for holding the at least one receptacle and the collecting device holder and a base portion, wherein the rack portion is attached to the base portion by means of a substantially horizontal axis and the rack portion may be tilted with respect to the base portion about the axis between the first position and the second position. By providing a stand which may be tilted about an axis, a very simple yet effective design is achieved which is easy to use.

In an advantageous embodiment, the base portion comprises at least one upwardly directed prong having a tapered shape and adapted to push the deflectable tab of the housing outwardly to release the snap-fit connection when the portable sampling device is placed on the base portion. By providing means for separating the housing from the collecting device holder, handling of the sampling device is made considerably easier in that the snap-fit connection is released virtually without effort by simply placing the sampling device on the base portion.

In an alternative embodiment, the stand is adapted to hold at least two, preferably at least three, receptacles parallel to each other and each coaxially aligned with a corresponding flow path of the collecting device holder. In the case of multiple collecting devices, the stand is adapted to transfer each collecting device to a separate receptacle, further facilitating handling and transferring of multiple samples from the sampling device to suitable receptacles simultaneously. This solution considerably reduces the time and effort needed to simultaneously handle a plurality of samples.

In a further preferred embodiment, the at least one receptacle is a test tube and/or a collection container with a closable lid. By adapting the stand to hold different kinds of receptacles, samples for different uses are prepared directly in the suitable receptacle without requiring subsequent transfer between receptacles.

In a third aspect of the present invention, there is provided a kit comprising a portable breath sampling device according to the first aspect and a stand according to the second aspect.

In a fourth aspect of the present invention, there is provided a tool for removal of a collecting device from a receptacle comprising gripping means arranged on a distal end for engaging an end of the collecting device and means for suspending the tool on a circumferential top edge of the receptacle. The tool facilitates handling and removal of a collecting device from the receptacle, such as a test tube, once eluent fluid has been added to release the collected particles from the collecting device through the process of elution. By suspending or hanging the tool gripping the collecting device on a top edge of the receptacle, the tool allows to let any remaining drops of eluent fluid to drip off. Eluent fluid is expensive and the tool ensures that as much as possible of the fluid is recovered in the receptacle, thereby reducing the total amount of eluent fluid needed.

In a preferred embodiment, the suspension means comprises a distally oriented hook arranged at a predetermined distance from the distal gripping means and adapted to engage the top edge of the receptacle. The hook is a simple and effective way of hanging the tool on the side of the receptacle and the distance may be adapted to the axial length of the collecting device and amount of eluent fluid used such that the distal end of the collecting device is suspended above the surface of the eluent fluid in the receptacle.

In an alternative embodiment, the gripping means comprise fork-like resilient tines adapted to engage an interior wall of the collecting device. Preferably, the width of the tines is adapted to the inner diameter of the collecting device such that they are somewhat deflected inwardly when the tool is inserted into the collecting device. Advantageously, each tine comprises a notch or indentation to provide a stop for the collecting device.

In a fifth aspect of the present invention, there is provided a kit comprising a portable breath sampling device according to the first aspect, a stand according to the second aspect and a tool according to the fourth aspect.

In a sixth aspect of the present invention, there is provided a method for collecting and analysing particles in exhaled breath comprising the steps:

collecting particles from a stream of exhaled breath using a portable sampling device according to the first aspect;
separating the collecting device holder from the housing;
fixing the collecting device holder in a stand according to the second aspect, with the stand in the first position;
fixing at least one receptacle coaxially aligned with the at least one flow path of the collecting device holder; and
bringing the stand from the first position to the second position such that the at least one collecting device is transferred from the collecting device holder to the receptacle by means of gravity.

In a preferred embodiment, the method further comprises the steps of:

adding an eluent fluid to the receptacle;
shaking the receptacle to release the collected particles from the collecting device;
removing the collecting device from the receptacle and discarding the collecting device.

In one embodiment the step of removing the collecting device from the receptacle comprises the steps of:

gripping the collecting device by means of a tool according to the third aspect;
suspending the tool and the collecting device on a top edge of the receptacle above the eluent fluid to allow remaining eluent fluid to drip off; and
removing and discarding the tool and the collecting device.

By the steps of the method incorporating the portable sampling device and stand or the portable sampling device, stand and tool according to aspects of the present invention, taking of a sample, handling the sample and analysing the sample is facilitated compared to known techniques. The simplicity and ease of use helps medical personnel to minimise risks of contamination and mishandling of collected samples and reduces time and effort in taking and preparing samples for analysis. Also costs may be reduced since the amount of eluent fluid required to extract the collected particles from the collecting device is reduced compared to known techniques.

BRIEF DESCRIPTION OF DRAWINGS

The invention is now described, by way of example, with reference to the accompanying drawings, in which.

DETAILED DESCRIPTION OF EMBODIMENTS

In the following, a detailed description of a portable sampling device, a sampling device stand and a gripping tool according to the invention is presented. In the drawing figures, like reference numerals designate identical or corresponding elements throughout the several figures. It will be appreciated that these figures are for illustration only and are not in any way restricting the scope of the invention.

Figure 1:
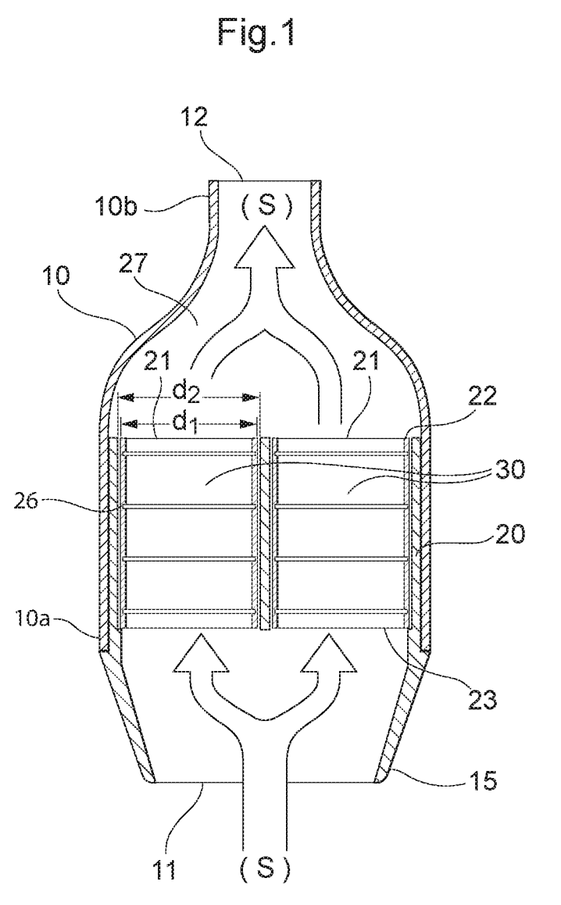
FIG. 1 shows a perspective view of a portable sampling device according to a first embodiment of the invention according to the first aspect in an assembled but operable state.
Figure 2:
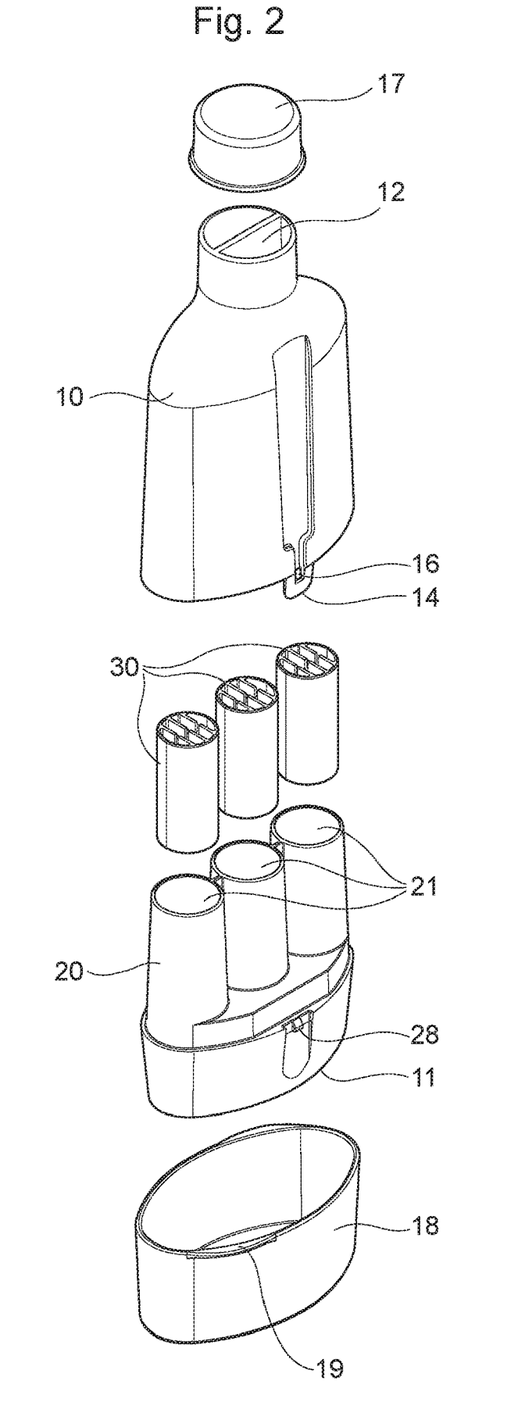
FIG. 2 shows an exploded view of a sampling device according to a second embodiment of the invention according to the first aspect, wherein the individual components are illustrated in a disassembled state.
Figure 3:
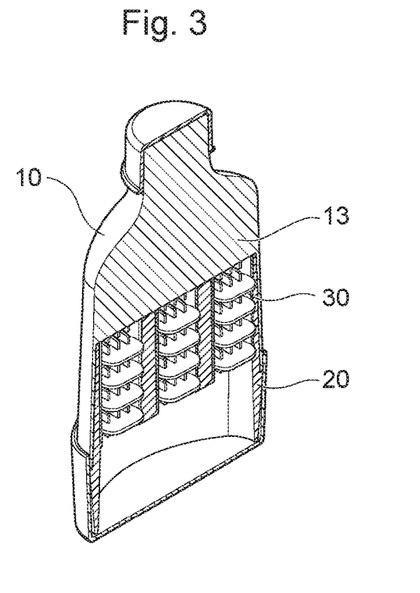
FIG. 3 shows a cross-sectional view of the assembled sampling device according to the second embodiment of the invention according to the first aspect.
Figure 4:
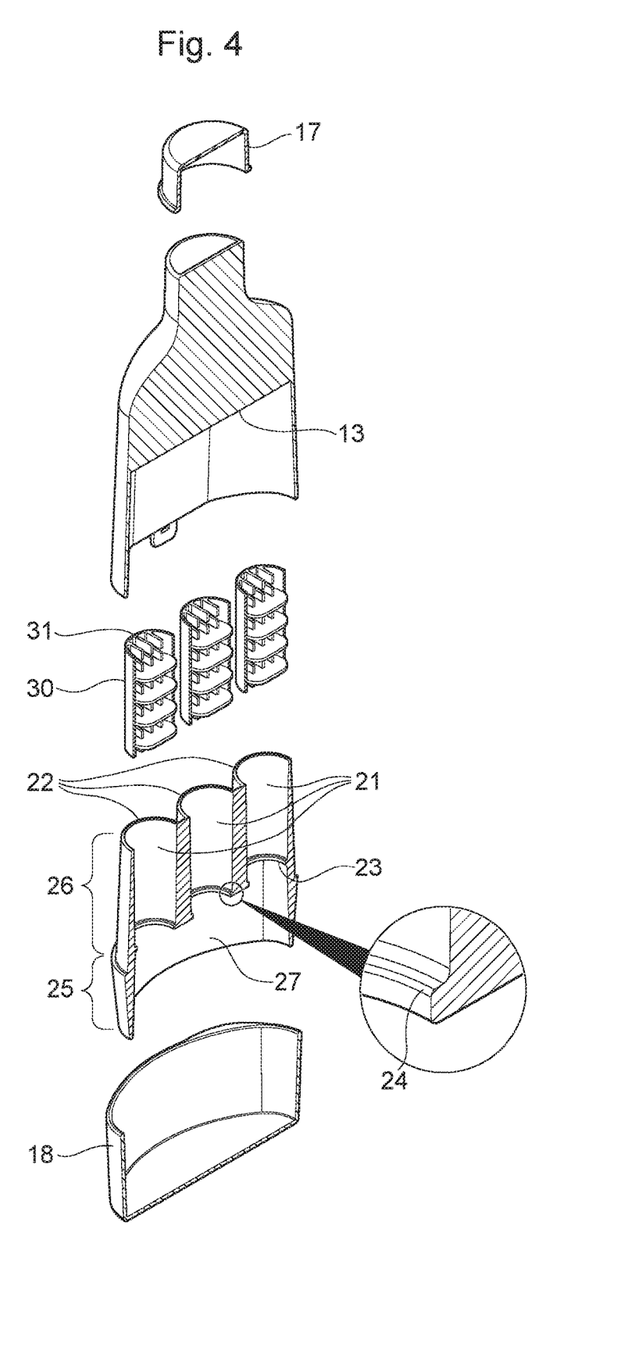
FIG. 4 shows a cross-sectional view of the disassembled sampling device in FIG. 2.

FIG. 1 shows in a perspective view a portable sampling device 1 according to a first embodiment the present invention in an assembled but operable state. FIG. 2 shows a portable sampling device 1 according to a second embodiment of the invention in an exploded view of the components of the sampling device 1. Furthermore, FIGS. 3 and 4 show cross-sectional views of the sampling device according to the second embodiment in FIG. 2 taken along a longitudinal axis of the sampling device in the direction of flow of exhaled breath. In the context of the present invention, the term 'portable sampling device' shall be interpreted as referring to a stand-alone, handheld device which may be carried and used by hand by a user. The sampling device 1 is adapted to be used for collecting particles in a stream of exhaled breath, as outlined above.

The sampling device 1 comprises an inlet 11 at a first, proximal end and an outlet 12 at a second, distal end. The terms proximal and distal when referring to the sampling device 1 should be interpreted as indicating the portion closest to and furthest away from the user, respectively, when blowing into the sampling device 1. Other terms may be used herein to describe different portions of the sampling device 1, such as upstream and downstream, which relate to the direction of flow (S) of the exhaled breath when the user blows into the sampling device 1. The terms upper and lower side of the sampling device 1 may also be used. The terms upper and lower side of the sampling device relate to the sides located closest to the nose or chin, respectively, when the inlet 11 is located in the user's mouth during the sampling procedure. The inlet 11 is formed as a mouthpiece arranged to receive the exhaled breath from the user and directing towards the outlet 12. The mouthpiece may in one embodiment have an oval shape in order to better fit into the mouth of the user. The sampling device further comprises an outer or external housing 10 comprising a first, proximal and a second, distal housing end 10a, 10b. The outlet 12 is arranged in said second, distal housing end 10b.

In order to collect the particles in the exhaled breath, the sampling device 1 further comprises at least one collecting device 30, movably arranged in a collecting device holder 20, which in turn is removably arranged at least partially inside the housing 10. The first, proximal housing end 10a of the housing 10 is adapted to receive the holder 20 to ensure a substantially airtight fit between the housing 10 and the holder 20, i.e. there is substantially no gap between the internal wall of the housing 10 and the external surface of the holder 20 such that substantially no part of the exhaled breath may pass there between. At least a proximal or upstream portion 25 of the holder 20 may remain outside the housing 10 when the sampling device 1 is assembled. The proximal portion 25 may have a greater width and/or thickness than the remaining distal or downstream portion 26 of the holder 20, such that the outer surface of the housing 10 is flush with the outer surface of the proximal portion 25.

In the distal portion 26 of the holder 20 there is provided at least two flow paths 21, in which the collecting device 30 is seated, in fluid connection with the inlet 11 to guide the stream of exhaled breath from the inlet 11 of the housing 10 through the holder 20 and the collecting device 30. The flow paths 21 may be of substantially cylindrical shape with a diameter d2, and the collecting device 30 may be in the form of a cylinder with a diameter d1, e.g. as disclosed in SE 1550930-0, which is hereby incorporated by reference in its entirety. The collecting device 30 hereby replaces the membrane filter used in the prior art and is adapted to collect aerosol particles, preferably aerosol particles consisting mainly of surfactant functioning as biomarkers, in exhaled breath. The collection device, as disclosed in SE 1550930-0, comprise at least four partition walls, arranged at a distance from each other and extending in a direction essentially perpendicular to the cylinder walls, partly covering the inner cross section of the collecting device. The aerosol particles are accumulated on said walls when the flow of exhaled breath interact with the walls when passing thorough the collecting devices 30 on its way from the inlet 11 to the outlet 12. Other shapes of the collecting device 30 may also be considered, as long as they can be movably arranged in the flow paths 21 to ensure easy removal without requiring extensive handling. The diameter d2 of the flow paths 21 is substantially smaller than the cross-sectional area of the holder 20 and of the housing 10. The remaining portion of the cross-sectional area of the holder 20 is formed with a wall, perpendicular to the flow path and direction of flow of exhaled breath through the sampling device 1 to prevent flow outside the flow paths 21. This decreased diameter of the flow paths 21 compared to the cross-sectional area of the housing 10 leads to an increased velocity of the flow of exhaled breath through the flow paths 21 and increased turbulence when passing through the collecting device 30, which is advantageous for the collection of aerosol particles in the exhaled breath. Another advantage is that it also allows for arrangement of more than two flow path 21 in the holder 20.

To ensure that the collecting device 30 is movably arranged in the flow path 21, the collecting device 30 has a diameter d1 which is smaller than the diameter d2 of the flow path 21, yet sufficiently big to minimise the gap between the outer surface of the collecting device 30 and the wall of the flow path 21 such that a major part, if not all, of the exhaled breath passes through the collecting device 30.

As may be seen in FIG. 1, which shows the assembled sampling device 1 in a cross-sectional view, the flow path 21 is arranged in a direction parallel to the direction of flow S of the exhaled breath through the sampling device 1. Further, the collecting device 30 is movably arranged in the direction of the flow path 21 such that the collecting device 30 may only be moved in relation to the holder 20 in this direction. This configuration allows for facilitated handling of the collecting device 30 once the particle sample from the exhaled breath has been collected. The operator can easily remove the collecting device 30 from the sampling device 1 by disassembling the holder 20 from the housing 10 and turning the holder 20 on end to let the collecting device 30 slide out by the force of gravity.

FIG. 4 shows a close-up view of the collecting device holder 20. As may be seen, the holder 20 has three cylindrical flow paths 21 arranged parallel and side-by-side. Having two or more parallel flow paths 21 is an advantage compared to known sampling devices, since it allows for simultaneous taking of multiple samples under identical conditions. Thus, one sample may be analysed at present and the other samples may be stored for future reference.

The flow paths 21 culminate or debouch into a common space 27 in the housing 10. The upstream or proximal end 23 of the each flow path 21 has retaining means in the form of an inwardly projecting annular flange 24 to hold the collecting device 30 in place after insertion. In other words, the collecting device 30 is movable in an downstream or distal direction of the holder 20, but may not move past the retaining flange 24. Other means of retaining the collecting device 30 may be foreseen, such as an obstruction in the form of bars, webbing or spokes extending across the flow path 21 perpendicular to the flow direction.

The housing 10 also comprises an abutment member for abutting against the collecting device 30 when the sampling device 1 is assembled. In FIG. 4, the housing 10 is shown in a cross-sectional view wherein an abutment member in the form of a partition 13 is seen extending in the longitudinal direction from the outlet 12 at the distal end of the housing 10. When the sampling device 1 is assembled, as shown in FIG. 3, the partition 13 extends in a proximal direction toward the distal end of the holder 20 and abuts against the distal end 31 of the collecting devices 30 arranged in the flow paths 21. As may be seen, the distal end 31 of each collecting device 30 is arranged flush with the distal end 22 of the flow path 21. It may also be foreseen that the longitudinal extension of the collecting device 30 is greater than that of the flow path 21. The partition 13 may in that case abut only against the distal end 31 of the collecting device. Also, the partition 13 need not extend the whole distance from the outlet 12, as long as it abuts against the collecting device 30. With this configuration, the collecting devices 30 are securely held in place in the assembled sampling device 1, but may easily be removed from the holder 20 when the housing 10 and holder 20 are separated from each other after completion of taking the sample from the exhaled breath. Other means of retaining the collecting device 30 may be foreseen, such as an obstruction in the form of webs or bars extending perpendicular against the flow direction S and abutting against the collecting devices 30.

Figure 5A:
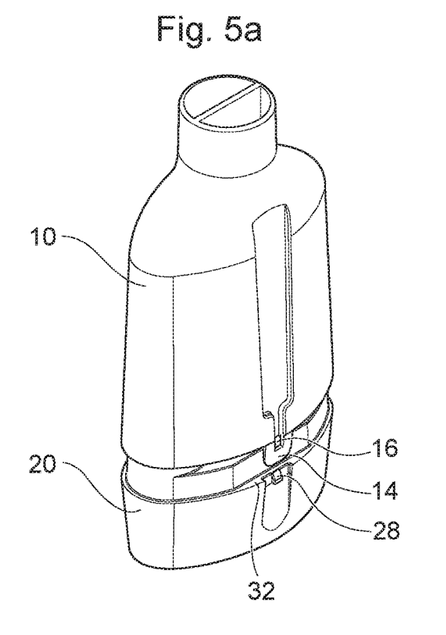
FIGS. 5a and 5b show details of the sampling device in non-assembled and assembled operative mode, i.e. without closures at the inlet and outlet.
Figure 5B:
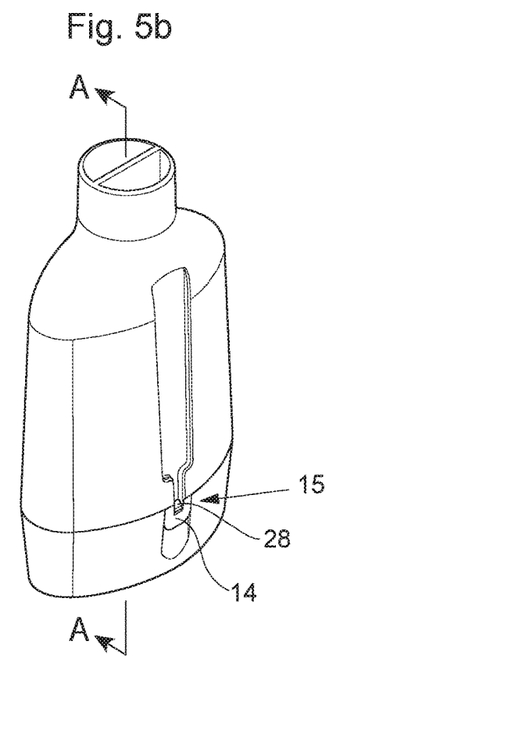

In order to ensure that the portable sampling device 1 has not been manipulated or tampered with, the housing 10 and collecting device holder 20 comprise corresponding complementary locking means which are adapted to be brought into engagement with each other when the housing 10 and holder 20 are assembled together to form the operative mode of the sampling device. One example of a locking means shown in FIGS. 5a and 5b is a cantilever snap-fit connection 15 wherein the housing 10 comprises a deflectable tab 14 including a recess 16 and the holder 20 comprises a cantilevered protrusion 28 configured to mate and engage with the recess 16. During assembly, the holder 20 containing the collecting devices 30 is brought into the housing 10. This causes the protrusion 28 to deflect the tab 14 outwardly until it snaps into a locking position, wherein the protrusion 28 is located in the recess 16, once the housing 10 and holder 20 have been fully assembled. The deflectable tab 14 may be manufactured such that any attempt to bend or tamper with the tab 14 to open the sampling device 1 will cause the tab 14 to bend or break off. Hence, the user and/or the operator will immediately see if the sampling device 1 has been manipulated prior to or during use. Locking means may be arranged on both sides of the housing 10 and holder 20, or only on one side.

The sampling device 1 further comprises a lid 17 to cover the outlet opening 12 of the housing 10, once a sample has been taken, in order to protect the sample from contamination. A lid 18 for the mouthpiece at the inlet opening 11 of the sampling device 1 may also be provided as shown in FIGS. 1 and 2. The lid 17 has outwardly directed flanges 19 to facilitate removal of the lid 18 from the sampling device.

The portable sampling device 1 according to the present invention is intended to be disposable for one-time use and therefore made from inexpensive, but medically acceptable material, such as plastic. Preferable materials include polypropylene (PP), polyvinylidene fluoride (PVDF), fluorinated ethylene propylene (FEP) and/or polytetrafluoroethylene (PTFE). Other materials such as metal or glass are also within the scope of the present invention.

Figure 6:
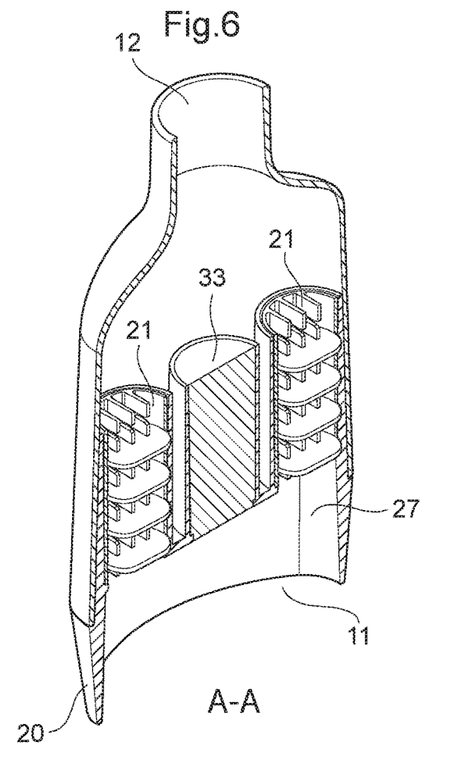
FIG. 6 shows a cross-sectional view taken along the cut A-A of a sampling device according to a modified second embodiment of the invention according to the first aspect.

In FIG. 6, there is shown an alternative design of the sampling device according to the first aspect of the invention, i.e. a sampling device comprising at least two flow paths 21 in fluid connection with the inlet 11. Here a holder 20 according to the second aspect, i.e. with three circular openings are used, but the centrally placed opening is closed off by a wall, insert or other type of closure 33. When closing off one of the openings the flow of breath S is divided in to two flow paths instead of three. This may be useful when a user is having difficulty to provide an exhalation through the device with enough flow to fill three collecting devices 30 with the sufficient amount of breath sample.

In one alternative embodiment, a device for measuring or visualising the amount of breath exhaled through the sampling device is arranged in connection to the outlet 12. Such a device may for example be a flow meter, an inflatable bladder or bag or other devices arranged to visualize a flow. When an insufficient exhalation rate is detected one of the flow paths may be closed off, for example by a plug in insert as shown in FIG. 6, to facilitate for the user to provide the sufficient flow through the device.

Figure 7:
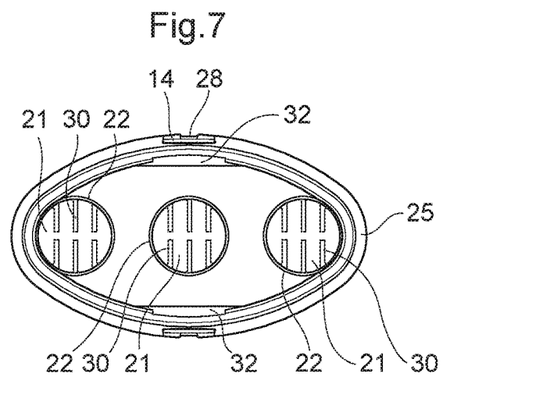
FIG. 7 shows a bottom view of FIG. 6.

FIG. 7 disclose a bottom view of the sampling device in FIG. 6. The housing 10 comprises at least one wall portion 32 protruding essentially perpendicular to the housing outer wall into the common space 27. The at least one wall portion 27 is arranged to protrude into the common space 27 and act as a saliva trap, preventing excessive amount of saliva and other large particle contamination, such as for example food, from entering the collecting devices 30. I.e. when the sampling device is arranged in the user's mouth, the wall portion 32 protrude into common space 27 from the lower side of the device in order to stop the particles heavier and larger than exhaled air with the sufficient amount of surfactant. If at least two opposite wall portions 27 are used, the device 1 do not have to have a predefined upper and lower side. In the embodiment shown in FIGS. 5a and 7 the wall portion 32 is an integrated part of the housing 20 designed as a step.

Figure 8:
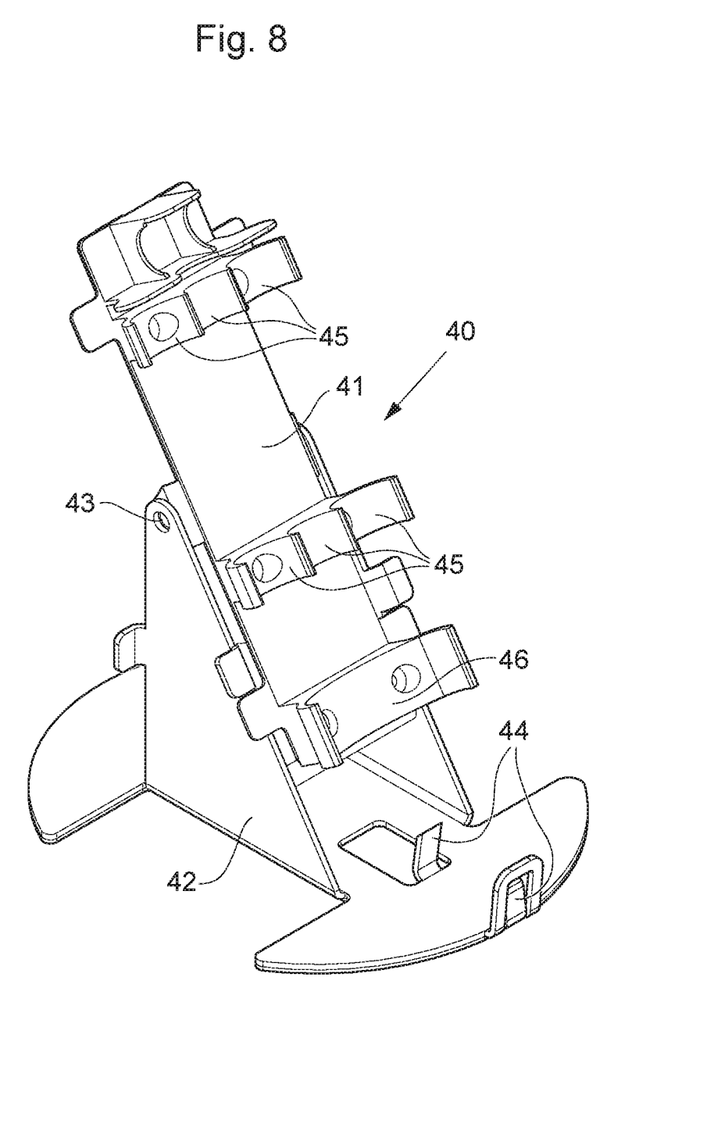
FIG. 8 shows a perspective view of a stand for a portable sampling device according to a second aspect.
Figure 9A:
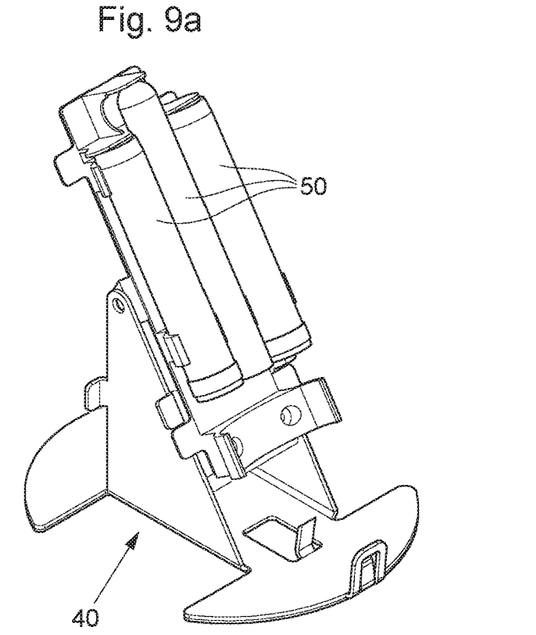
FIGS. 9a-9c show different steps employed in a method according to a sixth aspect.

In FIG. 8, there is shown a stand 40 according to a second aspect to be used together with a portable sampling device 1 according to the first aspect. The stand 40 comprises one or more grooves or recesses 45 adapted to hold one or more receptacles 50 for receiving a collecting device 30 carrying a sample of particles from an exhaled breath. The receptacle 50 may be a test tube or any other suitable container of preferably cylindrical shape. In FIG. 9a, three receptacles 50 are shown, a test tube in the middle position and cylindrical collection containers with closable lids (not shown) on either side. Further, the stand 40 comprises a recess 46 adapted to hold the collecting device holder 20 in a configuration such that the receptacles 50 are coaxially aligned with the one or more flow paths 21 of the holder 20.

The stand 40 is made to be movable between a first position and a second position. Advantageously, the portion of the stand 40 holding the receptacles 50, i.e. the rack portion 41, is attached to a base portion 42 via a substantially horizontal axis 43 at a centre point located substantially halfway along the longitudinal extension of the rack portion 41. The axis 43 is substantially perpendicular to the longitudinal extension of the rack portion 41 and the rack portion 41 may be tilted in relation to the base portion 42 about the axis 43 to bring the stand 40 from the initial, first position shown in FIG. 9a to the final, second position shown in FIG. 9c.

The purpose of tilting the stand 40 from the first position to the second position is to transfer the collecting devices 30, movably arranged in the holder 20, to the receptacles 50 without requiring direct handling of the collecting devices 30 by the operator. Thus, the risk of contamination or mishandling of the collecting devices 30 is greatly reduced, if not completely eliminated.

Figure 9B:
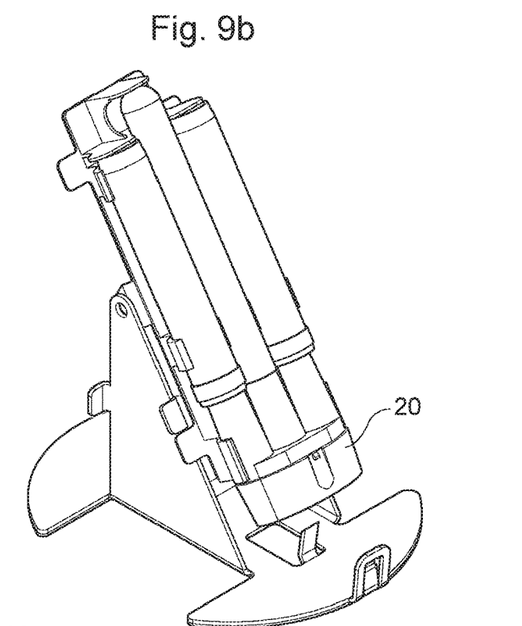
Figure 9C:
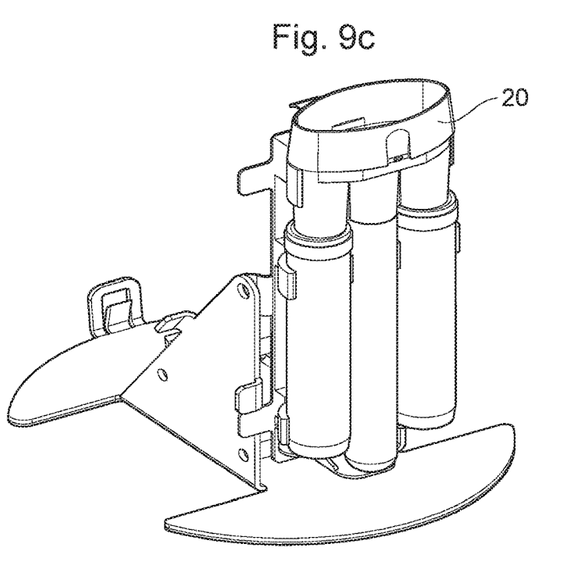

In use, the operator removes the lids 17, 18 and separates the outer housing 10 from the holder 20 containing the collecting devices 30 after a breath sample has been taken. Then, the operator places the required number of receptacles 50 in the stand 40 being in the first position, as shown in FIG. 9a. Next, the holder 20 is placed on the stand 40 such that the inlet openings 22 of each flow path 21 are coaxially aligned with respective openings of the receptacles 50 held in the rack portion 41 of the stand 40, as shown in FIG. 9b. In this first position, the holder 20 is arranged directly below the receptacles 50 and the collecting devices 30 are retained in the flow paths 21 by the inwardly directed flanges 24. Then, the rack portion 41 is tilted with respect to the base portion 42 about the axis 43 to the second position such that the holder 20 and receptacles 50 are turned upside down, with the holder 20 now being arranged directly above the receptacles 50, as shown in FIG. 9c. Since there is nothing retaining the collecting devices 30 at the proximal inlet openings 22 of the flow paths 21, the effect of gravity causes the collecting devices 30 to fall down into the respective receptacles 50.

Figure 10:
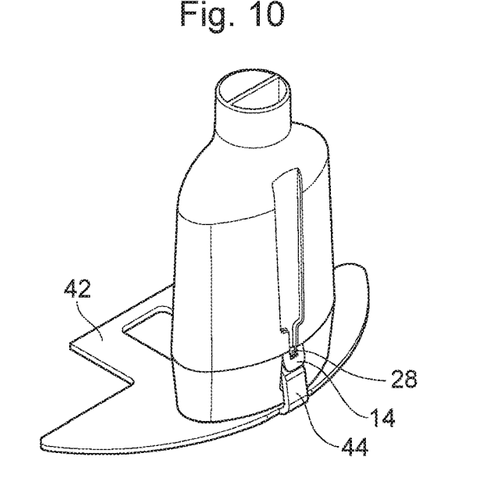
FIG. 10 shows a cut-away portion of the stand illustrating disassembly of the portable sampling device.

In order to further facilitate handling of the sampling device 1 after a sample has been collected, the base portion 42 of the stand 40 comprises means for separating the housing 10 from the collecting device holder 20, i.e. for opening the locking means holding the housing 10 and holder 20 together. As shown in FIG. 8, the base portion 42 comprises upwardly directed prongs 44 arranged to engage the snap-fit connection 15 on the housing 10 and holder 20. More specifically, the prongs 44 of the base portion 42 are tapered such that when the sampling device 1 is placed on the base portion 42, as shown in FIG. 10, the deflectable tabs 14 of the housing 10 come into contact with the prongs 44 and are pushed outwardly, thereby releasing the engagement with the protrusions 28 of the holder 20. Once the snap-fit connection 15 between the housing 10 and the holder 20 is released, the housing 10 may be lifted off, and the holder 20 may be placed in the rack portion 41 as described above, and shown in FIGS. 9*a-c*.

After the collecting devices 30 have been transferred to the receptacles 50, an eluent or extraction fluid may be added to the test tube in order to extract the sample particles through the process of elution. The eluent acts as a solvent to wash the sample particles from the walls of the collecting device 30. After adding of the eluent, the test tube is shaken in order to loosen (elute) as many particles as possible from the collecting device 30. Finally the collecting device 30 is removed from the test tube.

Figure 11:
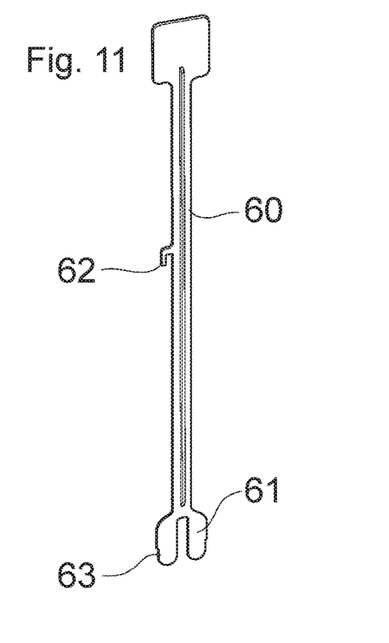
FIG. 11 shows a tool according to the fourth aspect.
Figure 11A:
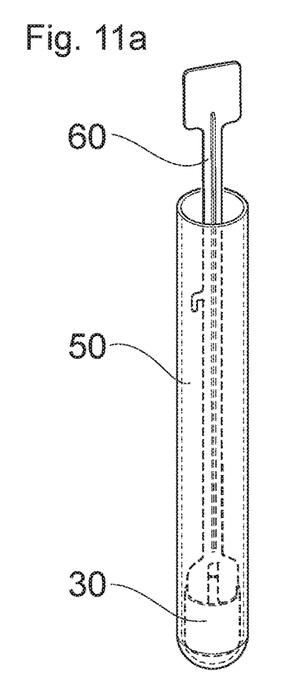
FIGS. 11a and 11b show the tool in FIG. 11 in use.

To this end, a tool 60 is provided which is adapted to grip the collecting device 30. The tool 60 is shown in FIG. 11 and comprises gripping means, e.g. in the shape of a fork with resilient tines or prongs 61, arranged on a distal end thereof for engaging one end of the collecting device 30, and means for suspending the tool 60 on a top edge of the test tube. The width of the tines 61 is adapted to the inner diameter of the collecting device 30 such that they are somewhat deflected inwardly when the tool 60 is inserted into the collecting device 30. The resilient nature of the tines 61 is due to the shape and resiliency of the material of the tool 60, preferably a plastic material such as polypropylene (PP), polyvinylidene fluoride (PVDF), fluorinated ethylene propylene (FEP) and/or polytetrafluoroethylene (PTFE). Each tine 61 may have a notch or indentation 63 to provide a stop for the collecting device 30. To remove the collecting device 30 from the receptacle 50, the tool 60 is introduced into the receptacle such that the tines 61 engage and hold the collecting device 30, as shown in FIG. 11*a*, and both are subsequently withdrawn and discarded together.

Figure 11B:
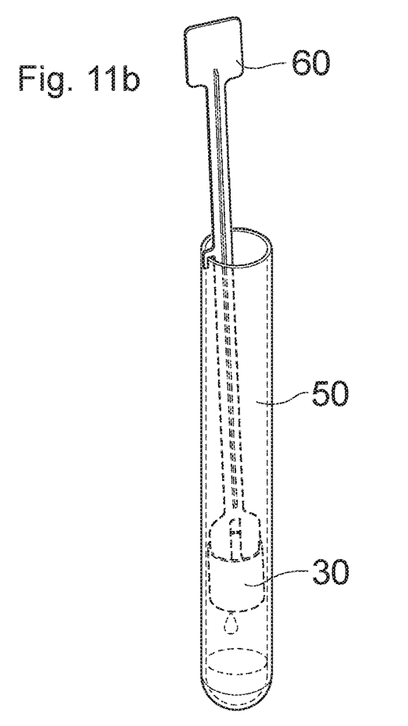

Since the eluent fluid is expensive, it is preferable that most, if not all, of the eluent fluid containing the extracted particles (also called eluate) is recovered. This also ensures that as many of the collected particles as possible are recovered for subsequent analysis. For recovery, the eluate is allowed to drip off the collecting device 30 before discarding the latter. By suspending the gripping tool 60 on the edge of the test tube as shown in FIG. 11*b*, the operator can leave the collecting device 30 suspended in place for a longer time to allow for the eluate to drip off, without needing to hold the gripping tool 60. In this way, a plurality of collecting devices 30 may be suspended on respective test tubes more or less simultaneously to allow for drip-off of the eluate, thus ensuring efficient handling of the collecting devices 30 and maximising the amount of eluate.

The suspension means comprises a distally oriented hook 62 arranged at a predetermined distance from the distal gripping means and adapted to engage the top edge of the receptacle 50. The distance between the hook 62 and the gripping means is adapted such that when the gripping tool 60 is suspended on the edge of the test tube, the collecting device 30 is raised above the surface of the eluate in the test tube, as shown in FIG. 11*b*.

Preferred embodiments of a portable sampling device for collecting particles, a stand for such a portable sampling device and a tool according to the invention have been described. However, the person skilled in the art realises that this can be varied within the scope of the appended claims without departing from the inventive idea.

All the described alternative embodiments above or parts of an embodiment can be freely combined without departing from the inventive idea as long as the combination is not contradictory.

The invention claimed is:

1. A portable sampling device for collecting aerosol particles in a stream of exhaled breath comprising:
- an inlet and an outlet,
- a housing; and
- a collecting device holder removably arranged at least partially inside the housing,
- wherein the sampling device is dimensioned to fit in the hand of a user,
- wherein the housing and holder are arranged to guide the stream of exhaled breath through the device from the inlet to the outlet,
- wherein the collecting device holder comprises at least two flow paths in fluid connection with the inlet, arranged side-by-side and extending parallel to a longitudinal axis of the sampling device in a downstream direction from the inlet towards the outlet,
- wherein a collecting device is arranged in each flow path, each collecting device being adapted to collect the aerosol particles in the exhaled breath,
- wherein the collecting device has a diameter smaller than the flow path diameter and is movably arranged in the collecting device holder.

2. The portable sampling device according to claim 1, wherein the collecting device is movably arranged in a direction parallel to the flow path in the collecting device holder.

3. The portable sampling device according to claim 1, wherein each flow path has a cylindrical shape and the collecting device holder comprises an inwardly directed flange at a proximal end of each flow path for retaining the collecting device in an upstream direction in the flow path of the collecting device holder.

4. The portable sampling device according to claim 3, wherein the housing comprises an abutment member adapted to abut against a distal end of each collecting device when the collecting device holder is arranged inside the housing.

5. The portable sampling device according to claim 1, wherein the collecting device holder comprises three flow paths arranged side-by-side and parallel to each other.

6. The portable sampling device according to claim 1, further comprising a cantilever snap-fit connection including at least one deflectable tab comprising a recess arranged on the housing and at least one cantilevered protrusion arranged on the holder, wherein the at least one protrusion is adapted to mate with and engage the recess in the at least one deflectable tab when the housing and the holder are brought together.

7. The portable sampling device according to claim 1, further comprising at least one lid to cover the inlet and/or the outlet of the sampling device.

8. The portable sampling device according to claim 7, wherein the at least one lid comprises at least one outwardly directed flange.

9. The portable sampling device according to claim 1, wherein the sampling device is disposable.

10. The portable sampling device according to claim 1, wherein the sampling device is made from a medically acceptable plastic material chosen from polypropylene, polyvinylidene fluoride (PVDF), fluorinated ethylene propylene (FEP) and/or polytetrafluoroethylene (PTFE).

11. The portable sampling device according to claim 1, each collection device is in the form of a cylinder with a diameter and comprises at least four partition walls, arranged at a distance from each other and extending in a direction essentially perpendicular to the cylinder walls, partly covering the inner cross section of the collecting device.

\* \* \* \* \*